United States Patent
Tollini et al.

(10) Patent No.: US 10,758,671 B2
(45) Date of Patent: Sep. 1, 2020

(54) SECUREMENT DEVICE ASSEMBLY AND SECUREMENT AND DRESSING DEVICE ASSEMBLY AND METHOD OF APPLYING SAID DEVICE ASSEMBLIES

(71) Applicant: TNT Moborg International Limited, Williamsville, NY (US)

(72) Inventors: Dennis R. Tollini, Clarence Center, NY (US); Michael D. Tollini, Clarence Center, NY (US)

(73) Assignee: TNT Moborh International Limited, Williamsville, NY (US)

( * ) Notice: Subject to any disclaimer, the term of this patent is extended or adjusted under 35 U.S.C. 154(b) by 345 days.

(21) Appl. No.: 15/584,689

(22) Filed: May 2, 2017

(65) Prior Publication Data
US 2017/0246387 A1    Aug. 31, 2017

Related U.S. Application Data

(63) Continuation-in-part of application No. PCT/US2016/020075, filed on Feb. 29, 2016.

(51) Int. Cl.
*A61M 5/158* (2006.01)

(52) U.S. Cl.
CPC ..... *A61M 5/158* (2013.01); *A61M 2005/1586* (2013.01)

(58) Field of Classification Search
CPC .......... A61M 2005/1586; A61M 5/158; A61M 25/02; A61M 31/002; A61M 5/14276; A61M 5/1723; A61B 17/12022; A61B 17/1204; A61B 17/12099; A61B 17/12136; A61B 17/12159; A61B 17/12163; A61B 17/12172; A61B 17/1219; A61B 2017/00119; A61B 2017/00221; A61B 2017/22069; A61B 5/065; A61F 5/0079
See application file for complete search history.

(56) References Cited

U.S. PATENT DOCUMENTS

| | | | |
|---|---|---|---|
| 2,807,262 A | 9/1957 | Lew | |
| 2,821,194 A * | 1/1958 | Simmons | A61M 25/02 604/180 |
| 3,288,136 A | 11/1966 | Lund | |
| 3,826,254 A | 7/1974 | Mellor | |
| 3,834,380 A | 9/1974 | Boyd | |
| 4,702,736 A | 10/1987 | Kalt et al. | |
| 4,704,177 A | 11/1987 | Vaillancourt | |
| 4,738,662 A | 4/1988 | Kalt et al. | |
| 4,838,878 A | 6/1989 | Kalt et al. | |
| 5,037,397 A | 8/1991 | Kalt et al. | |

(Continued)

OTHER PUBLICATIONS

3M Critical & Chronic Care Solutions; 3M™ Micropore™ Tape 1530S-1 (3M ID 70200407446; UPC#30707387075553); 2014.

(Continued)

*Primary Examiner* — Brandy S Lee
(74) *Attorney, Agent, or Firm* — Simpson & Simpson, PLLC; Michael Nicholas Vranjes

(57) ABSTRACT

A securement device assembly, including an adhesive layer having a top surface and a bottom surface, wherein said adhesive layer includes at least two apertures, a non-adhesive substrate secured to said bottom surface of said adhesive layer to form an integral unit, and a plurality of perforations within said integral unit.

32 Claims, 10 Drawing Sheets

(56) References Cited

U.S. PATENT DOCUMENTS

| | | | |
|---|---|---|---|
| 5,086,763 A | 2/1992 | Hathman | |
| 5,098,399 A | 3/1992 | Tollini | |
| 5,147,322 A | 9/1992 | Bowen et al. | |
| 5,266,401 A | 11/1993 | Tollini | |
| 5,300,037 A | 4/1994 | Delk et al. | |
| 5,304,146 A | 4/1994 | Johnson et al. | |
| 5,496,605 A | 3/1996 | Augst et al. | |
| 5,520,656 A | 5/1996 | Byrd | |
| 5,562,107 A | 10/1996 | Lavender et al. | |
| 5,575,802 A | 11/1996 | McQuilkin et al. | |
| 5,681,290 A | 10/1997 | Alexander | |
| 6,132,399 A | 10/2000 | Shultz | |
| 6,689,105 B2 | 2/2004 | Tollini | |
| 7,659,439 B2 | 2/2010 | Grossman | |
| 2005/0015036 A1 | 1/2005 | Lutri et al. | |
| 2005/0043686 A1 | 2/2005 | Tollini | |
| 2006/0211994 A1* | 9/2006 | Roman | A61M 25/02 604/180 |
| 2008/0039760 A1 | 2/2008 | Lesko | |
| 2008/0154168 A1 | 6/2008 | Lutri | |
| 2010/0198161 A1* | 8/2010 | Propp | A61F 13/0269 604/180 |
| 2011/0098622 A1 | 4/2011 | Hatanaka et al. | |
| 2011/0152778 A1 | 6/2011 | Gyrn | |
| 2013/0116645 A1* | 5/2013 | Corley | A61L 15/26 604/369 |
| 2013/0310754 A1 | 11/2013 | Kutsch | |
| 2014/0005607 A1 | 1/2014 | Elsamahy et al. | |
| 2015/0224285 A1 | 8/2015 | Howell et al. | |

OTHER PUBLICATIONS

3M™ Tegaderm™ Transparent Film Dressing Family; Brochure; Copyright 2005; Published by 3M; St. Paul, MN, USA.

* cited by examiner

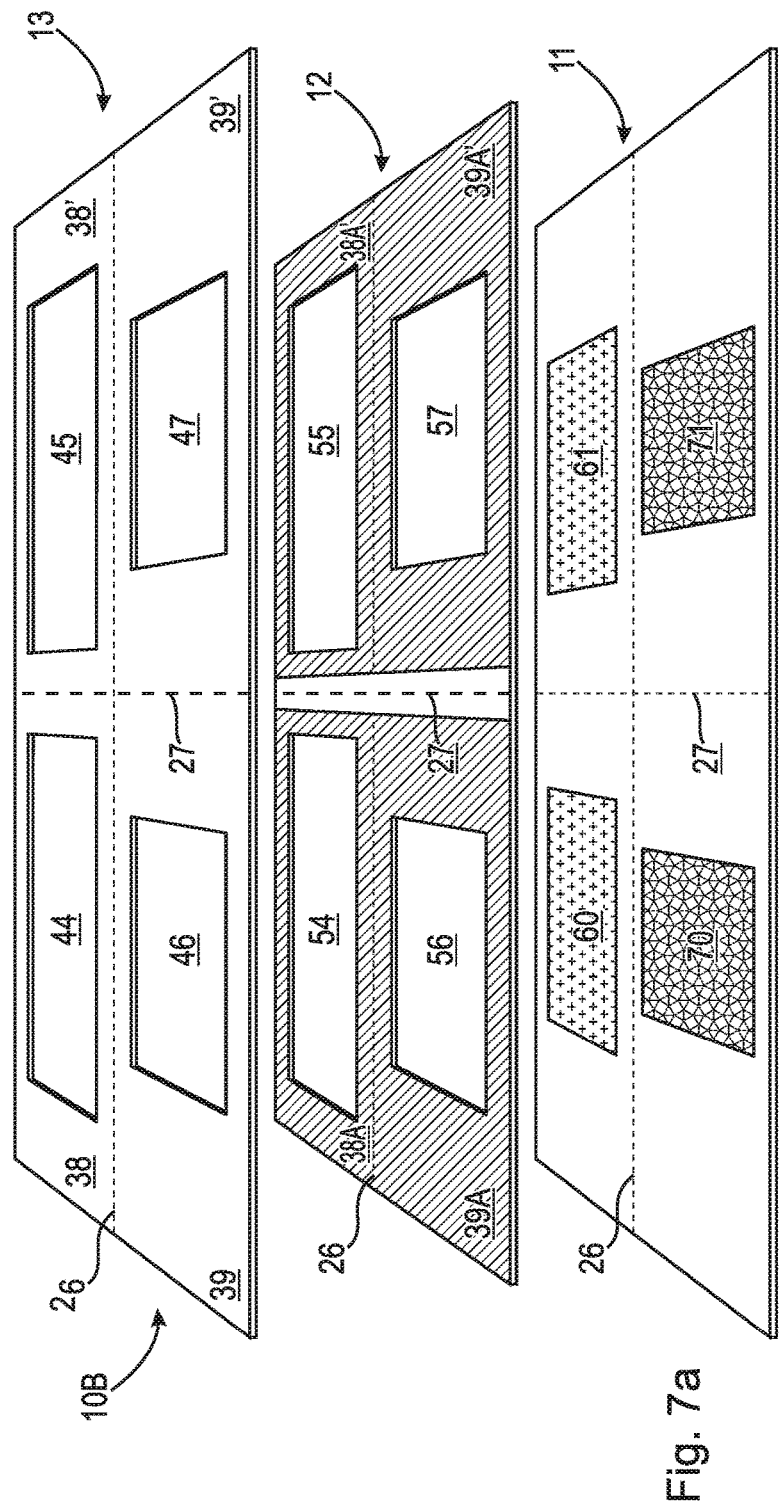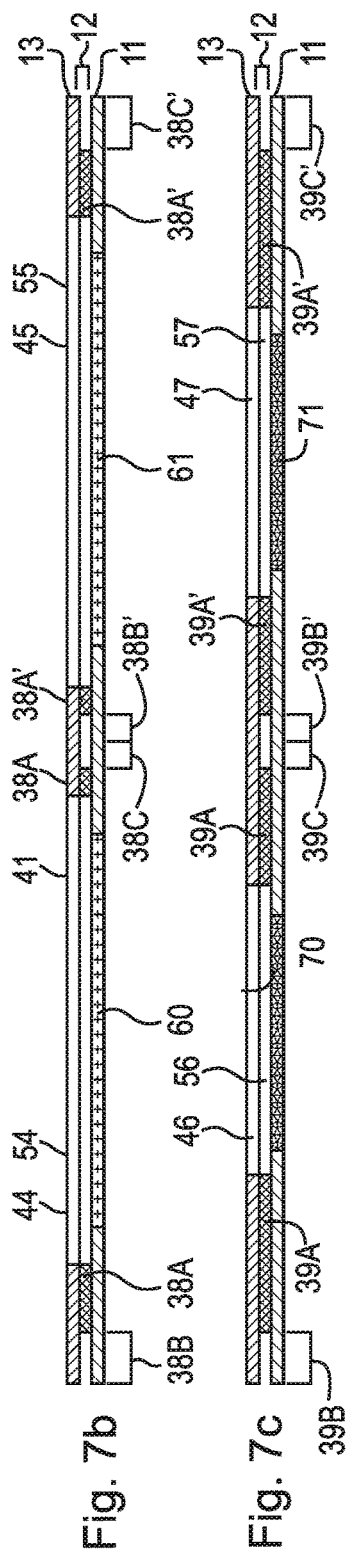

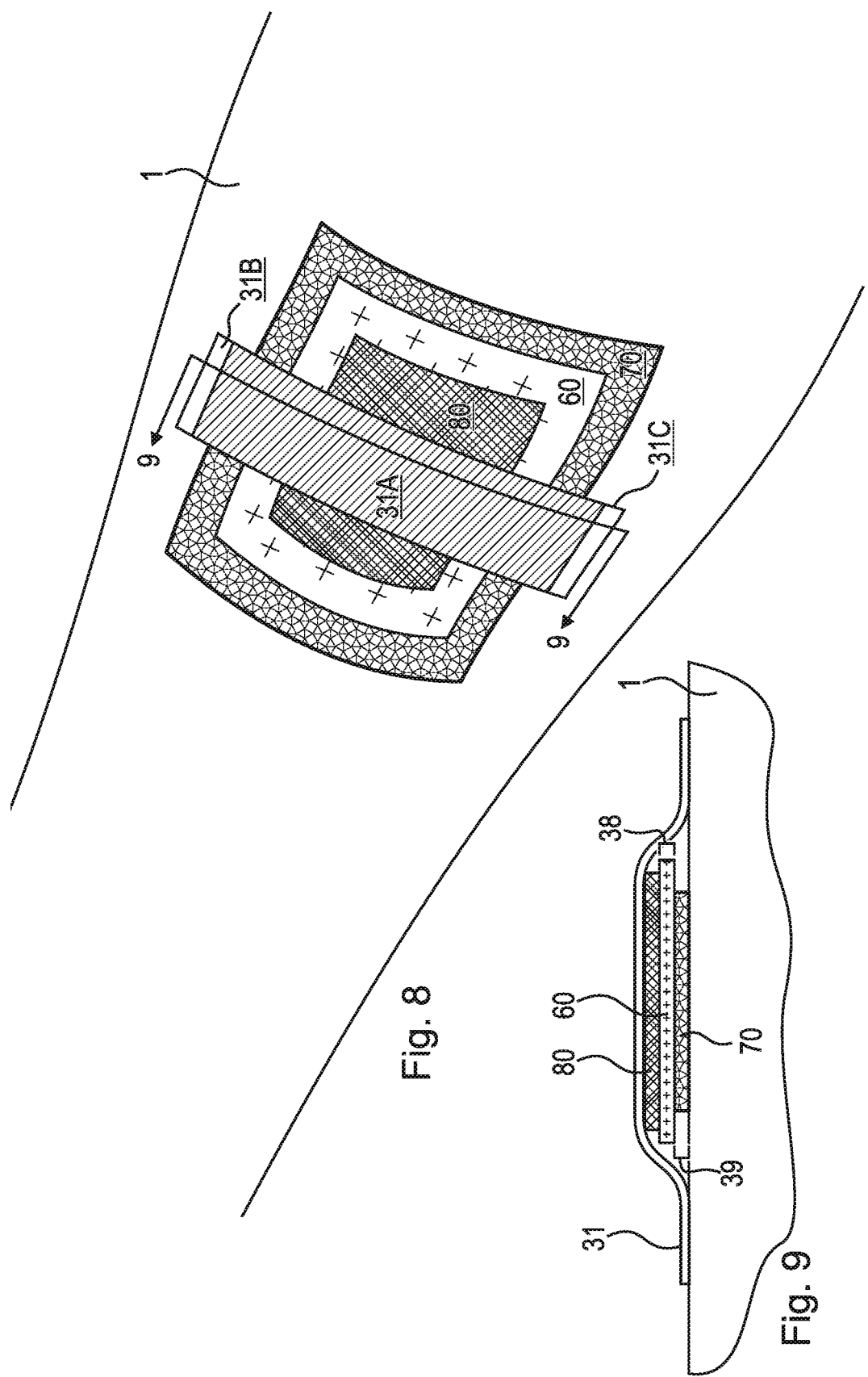

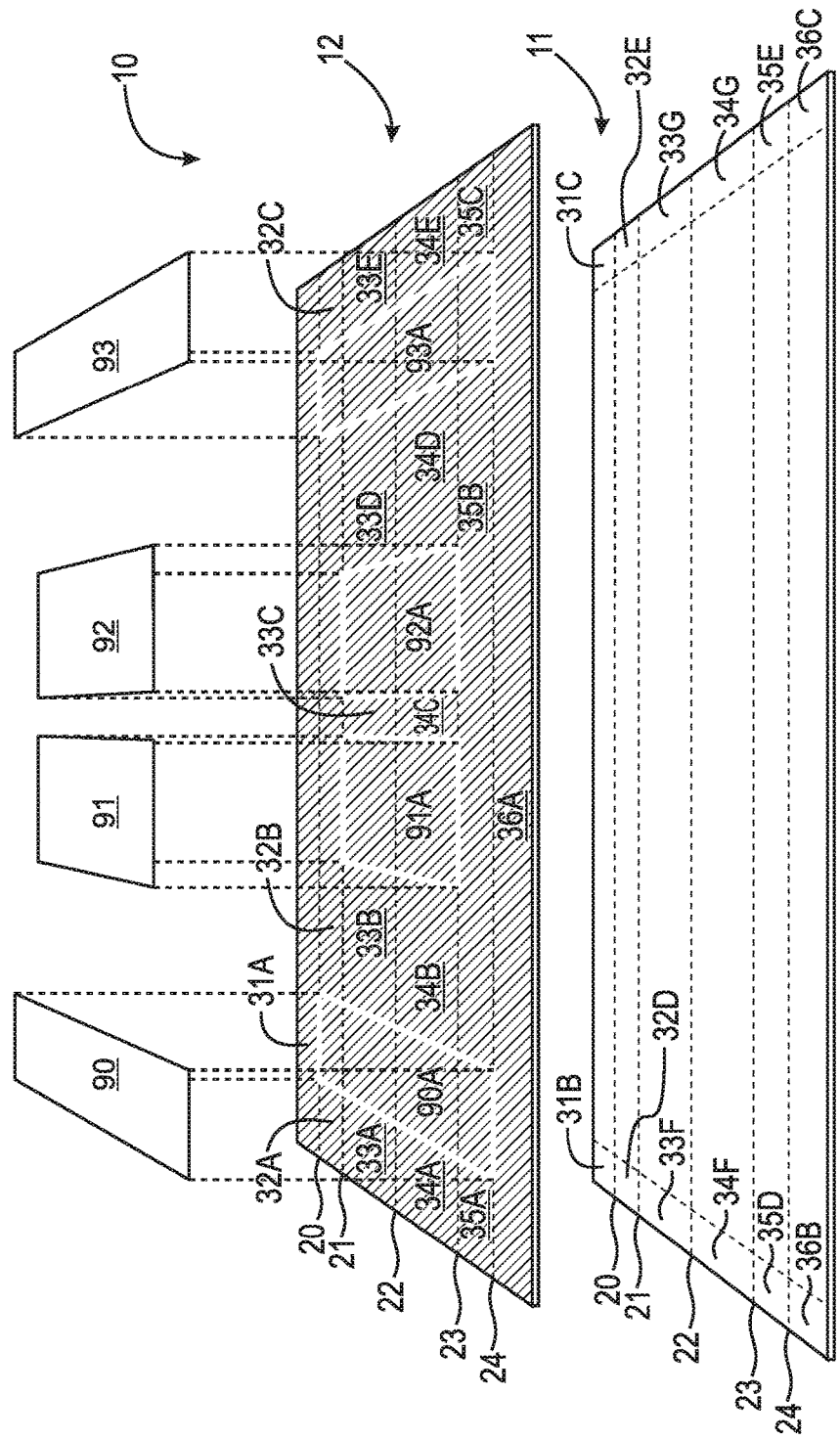
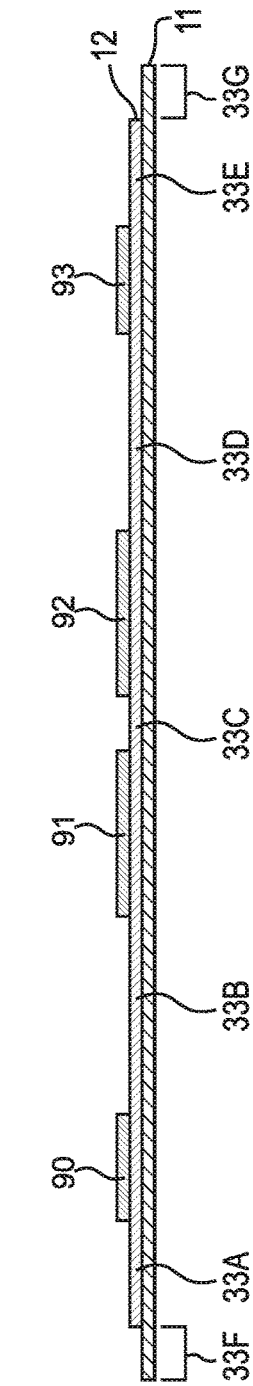
Fig. 10a
Fig. 10b

SECUREMENT DEVICE ASSEMBLY AND SECUREMENT AND DRESSING DEVICE ASSEMBLY AND METHOD OF APPLYING SAID DEVICE ASSEMBLIES

CROSS REFERENCE TO RELATED APPLICATIONS

This application claims priority under 35 U.S.C. § 120 and 35 U.S.C. § 365(c) as a continuation-in-part of PCT International Patent Application No. PCT/US2016/020075, filed Feb. 29, 2016, which application is incorporated herein by reference in its entirety.

FIELD

The invention relates generally to securement device assemblies, and, more particularly to assemblies that can be used as securement and dressing devices in the medical profession.

BACKGROUND

Securement devices are used in the medical profession to secure needles and catheters inserted within patients to prevent dislodgement, phlebitis, damage to surrounding tissue, and the ingress of bacteria at the insertion site, and damaging surrounding tissue. Medical grade tape can be used as a securement device or to supplement a securement device. Safe and effective securement devices are particularly critical for the treatment of chronic conditions, such as kidney failure, which requires constant dialysis treatment for removing waste from a patient's blood. For patients receiving routine hemodialysis, for example, an intravenous catheter is one method that may be used to gain access to the blood. Catheter access consists of a plastic catheter with two lumens which is inserted into a large vein to allow large flows of blood to be withdrawn from one lumen, to enter the dialysis circuit, and to be returned via the other lumen. The constant site technique is being increasingly employed, where a blunted needle is inserted in exactly the same site, so as to develop "buttonhole" accesses that may be used repeatedly. However, the skin surrounding a buttonhole access is continually irritated and is susceptible to infection. Since existing securement devices are primarily opaque, healthcare providers are unable to visualize the entire insertion site. Thus, tape application, removal, and reapplication can be cumbersome.

To expedite hemodialysis which can take hours to complete, efficient blood and dialysate flow rates are desired. To achieve optimal flow rates, needles or catheters often require adjustment, either at the onset of or at some point during treatment. Typically, to adjust a securement device, tape is removed and new tape is applied to and around the site further aggravating the skin.

Healthcare providers have struggled with providing securement devices that are effective and sterile yet minimally aggravating to patients.

United States Patent Application Publication No. 2010/0198161 (Propp) discloses a window dressing having an integral anchor. The window dressing disclosed includes a fabric layer having juxtaposed insertion site viewing and anchor member portions. The fabric layer has an adhesive side and an opposite non-adhesive side. The insertion site viewing portion is defined by an opening in the fabric layer. A transparent film layer having an adhesive skin-adhering side and an opposite non-adhesive side is adhered to the fabric layer adhesive side and closes the opening in the fabric layer. The anchor member portion includes a reinforcing structure disposed on the fabric layer and having an adhesive side and an opposite non-adhesive side. The reinforcing structure adhesive side is adhered to the fabric layer non-adhesive side such that the reinforcing structure is on top of the fabric layer. Unfortunately, the Propp reference discloses an assembly that is mostly opaque fabric having only a small opening through which the insertion site may be viewed. Moreover, the Propp reference discloses layers having sides which are either completely coated with adhesive or not coated at all.

U.S. Pat. No. 4,704,177 (Vaillancourt) discloses a medicator securing device utilizing a thin, transparent plastic film coated on one side with an adhesive and having a border frame at least along three sides. No adhesive is present on the exposed surfaces of the border frame and are available to be grasped so as to provide ready separation of the adhesive surfaces of the facing films when brought together. Unfortunately, the Vaillancourt reference discloses a sheet having sides which are either continuously coated with adhesive or not coated at all.

A latex-free, hypoallergenic paper tape is available from 3M Corporate Headquarters, 3M Center, St. Paul, Minn. 55144-1000 (3M ID 70200407446; UPC #30707387075553). However, the paper tape is opaque.

Therefore, there is a long-felt need for a completely transparent tape assembly having a non-adhesive substrate and an adhesive applied to some portions of the substrate while other portions of the substrate remain without adhesive. There is also a need for a tape assembly that is customizable for different needles or catheters.

SUMMARY

According to aspects illustrated herein, there is provided a securement device assembly, comprising an adhesive layer having a top surface and a bottom surface, wherein said adhesive layer includes at least two apertures, a non-adhesive substrate secured to said bottom surface of said adhesive layer to form an integral unit, and a plurality of perforations within said integral unit.

According to aspects illustrated herein, there is provided a securement and dressing device assembly, comprising an adhesive layer having a top surface and a bottom surface, wherein said adhesive layer includes at least two apertures, a non-adhesive substrate, comprising at least one absorption element secured to said non-adhesive substrate, and arranged in registration with a first of said apertures, and at least one permeable element secured to said non-adhesive substrate, and arranged in registration with a second of said apertures, wherein said non-adhesive substrate is secured to said bottom surface of said adhesive layer to form an integral unit, and a plurality of perforations arranged within said integral unit.

According to aspects illustrated herein, there is provided a method for securing a needle assembly to a person using a tape assembly, comprising the steps of inserting said needle assembly into a vessel of said person, said needle assembly comprising a tube connected to a needle and a wing fixedly secured thereto, adhering a first strip of material under said tubing proximate said wing of said needle, wherein said first strip of material has a first end and a second end, folding said first end and said second end of said first strip of material such that said first and second ends traverse said wing of said needle, adhering said first and second ends of said first strip of material to said person, and adhering a second strip of material atop of said wing and said first strip of material.

According to aspects illustrated herein, there is provided a securement and dressing device assembly, comprising an adhesive layer having a top surface and a bottom surface, wherein said adhesive layer includes at least two apertures, a non-adhesive substrate secured said bottom surface of said adhesive layer to form an integral unit, and a plurality of perforations operatively arranged within said integral unit, said plurality of perforations forming a first portion having a plurality of removable strips and a second portion having at least one absorption element and at least one permeable element.

According to aspects illustrated herein, there is provided a securement device assembly, comprising a non-adhesive substrate having a first top surface and a first bottom surface, an adhesive layer having a second top surface and a second bottom surface, said adhesive layer secured to said first top surface along said second bottom surface, a plurality of adhesive blockers arranged on the second top surface, wherein the non-adhesive substrate, the adhesive layer, and the plurality of adhesive blockers form an integral unit, and a plurality of perforations within said integral unit separating said integral unit into a plurality of sections.

The primary object of the invention is to provide a tape assembly which is completely transparent to allow for medical personal to observe a medical procedure.

A further object of the invention is to provide a tape assembly with adhesive in certain locations to allow for easy adjustment and readjustment of the tape assembly.

Yet another object of the invention is to provide a transparent tape assembly having a minimal amount of adhesive such that the tape assembly is effective yet minimally abrasive to the skin of a patient.

Another object of the invention is to provide a tape assembly for securing a needle within a patient's arm and for dressing the cannulation site after the needle has been removed.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 1b is a fragmentary exploded view of a first embodiment of the assembly shown in FIG. 1a;

FIG. 1c is a cross-sectional view of the first embodiment of the assembly taken generally along line 1a-1a in FIG. 1a;

FIG. 7a is a fragmentary exploded view of the assembly shown in FIG. 1a;

FIG. 7b is a cross-sectional view of the tape assembly taken generally along line 7b-7b in FIG. 1a;

FIG. 7c is a cross sectional view of the tape assembly taken generally along line 7c-7c in FIG. 1a;

FIG. 8 is a perspective view of the tape assembly dressed;

FIG. 9 is a cross sectional view of the dressing of the assembly shown in FIG. 8 taken generally along line 9-9 in FIG. 8;

FIG. 10a is a fragmentary exploded view of a second embodiment of the assembly shown in FIG. 1a; and, FIG. 10b is a cross-sectional view of the second embodiment of the assembly taken generally along line 1a-1a in FIG. 1a.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials, and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices, or materials similar or equivalent to those described herein can be used in the practice or testing of the example embodiments.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

Figure 1A:
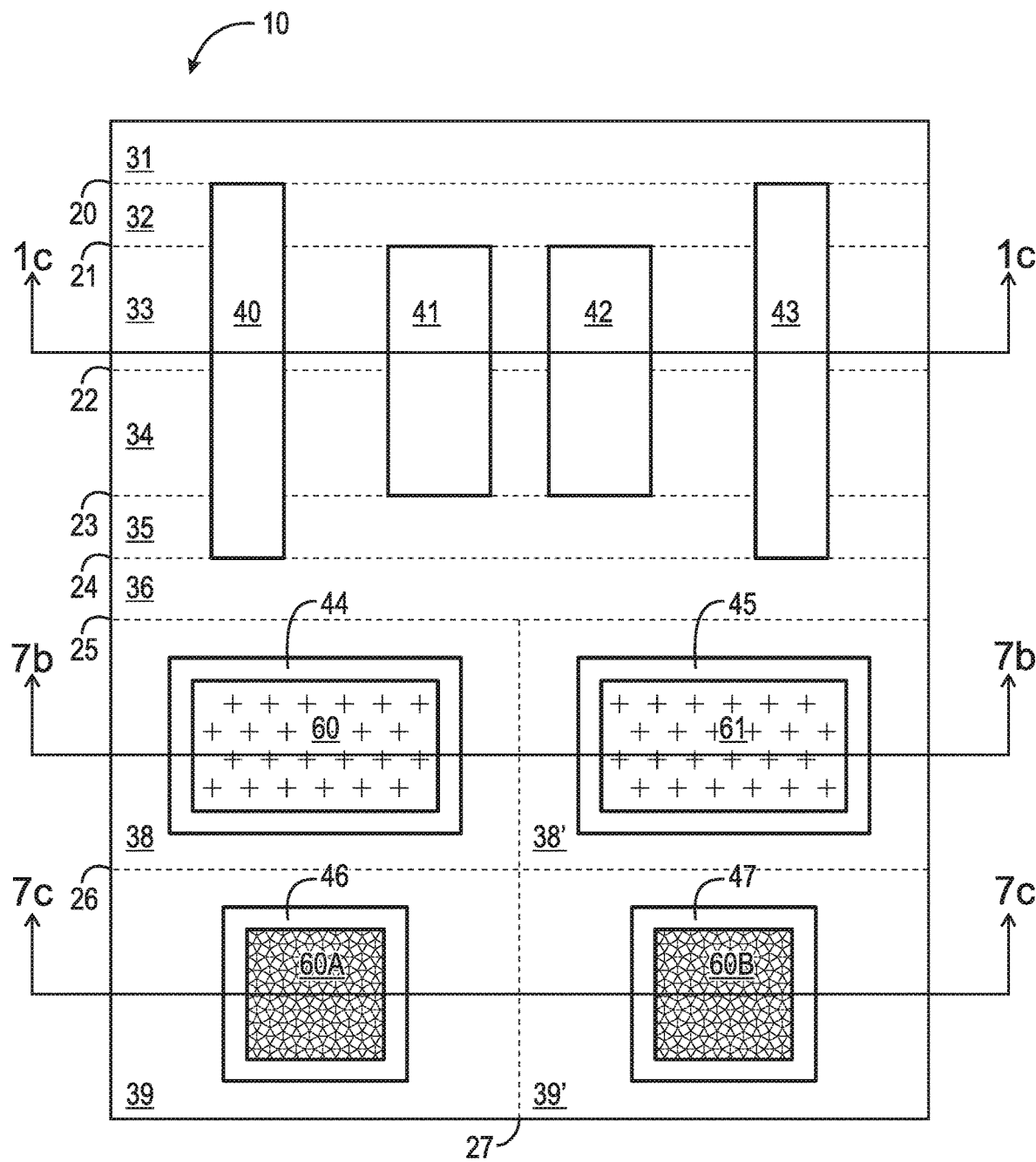
FIG. 1a is a top view of the assembly of the present invention.

Adverting now to the figures, FIG. 1a is a top view of assembly 10. Assembly 10 broadly includes, from bottom to top, transparent non-adhesive substrate 11, transparent adhesive layer 12, and removable layer 13. Of these three layers, only removable layer 13 is visible from the top view shown in FIG. 1a. When assembled, the bottom side of removable layer 13 is adhered to the top side of transparent adhesive layer 12, and the top side of transparent non-adhesive substrate 11 is adhered to the bottom side of transparent adhesive layer 12. Transparent non-adhesive substrate 11 and transparent adhesive layer 12 are arranged such that they remain adhesively joined. Removable layer 13 is arranged such that it is removable from transparent adhesive layer 12 and transparent non-adhesive substrate 11.

As shown in FIG. 1a, assembly 10 can include perforations. In a preferred embodiment, perforation lines 20, 21, 22, 23, 24, 25, 26, and 27 are included to separate assembly 10 into removable sections 31, 32, 33, 34, 35, 36, 38, 38', 39, and 39'. It should be appreciated that assembly 10 is divisible into removable sections 31, 32, 33, 34, 35, 36, 38, 38', 39, and 39' while transparent non-adhesive substrate 11, transparent adhesive layer 12, and removable layer 13 remain assembled. For example, if removable sections 31, 32, and 33 are separated from removable sections 34, 35, 36, 38, 38', 39, and 39' along perforation line 22, removable sections 31, 32, and 33 remain joined and include the corresponding portions of transparent non-adhesive substrate 11, transparent adhesive layer 12, and removable layer 13. Using the same example and same circumstances, sections 34, 35, 36, 38, 38', 39, and 39' remain joined and include the corresponding portions of transparent non-adhesive substrate 11, transparent adhesive layer 12, and removable layer 13.

Removable layer 13 includes apertures 40, 41, 42, 43, 44, 45, 46, and 47, and transparent adhesive layer 12 includes apertures 50, 51, 52, 53, 54, 55, 56, and 57. Said apertures represent the absence of material within removable layer 13 and transparent adhesive layer 12, respectively. FIG. 1a shows removable layer 13 apertures 40, 41, 42, 43, 44, 45, 46, and 47. Transparent adhesive layer 12 apertures 50, 51, 52, 53, 54, 55, 56, and 57, are aligned directly below, and are identical in size to, removable layer 13 apertures 40, 41, 42, 43, 44, 45, 46, and 47, respectively. In one embodiment, apertures are cut into removable layer 13 and transparent adhesive layer 12 after they have been secured together, but before transparent non-adhesive substrate 11 is assembled. This ensures that apertures 40, 41, 42, 43, 44, 45, 46, and 47 are precisely aligned with, and identical in size to, apertures 50, 51, 52, 53, 54, 55, 56, and 57, respectively. Thus, describing the dimensions and orientation of removable layer 13 apertures sufficiently describes the respective transparent adhesive layer 12 apertures. Aperture 40 extends from perforation line 20 to perforation line 24 and spans removable sections 32, 33, 34, and 35 of assembly 10. Aperture 43 is substantially similar to aperture 40, as it also extends from perforation line 20 to perforation line 24 and spans removable sections 32, 33, 34, and 35. In a preferred embodiment, apertures 40 and 43 are substantially parallel. Apertures 41 and 42 are located between apertures 40 and 43. Aperture 41 extends from perforation line 21 to perforation line 23 and spans removable sections 33 and 34. Aperture 42 is substantially similar to aperture 41, as it also extends from perforation line 21 to perforation line 23 and spans removable sections 43 and 44. In a preferred embodiment, apertures 41 and 42 are substantially parallel.

Also in a preferred embodiment, apertures 40, 41, 42, and 43 are substantially parallel. It is important to note, however, that perforation lines 20, 21, 22, 23, 24, 25, 26, and 27 and apertures 40, 41, 42, and 43 do not need to be parallel and can be of any shape. For example, perforation lines 20, 21, 22, 23, 24, 25, 26, and 27 could be represented by lines with an oscillating wave pattern and apertures 40, 41, 42, and 43 could be of any shape such as an oval or circle.

Figures 1B, 1C:
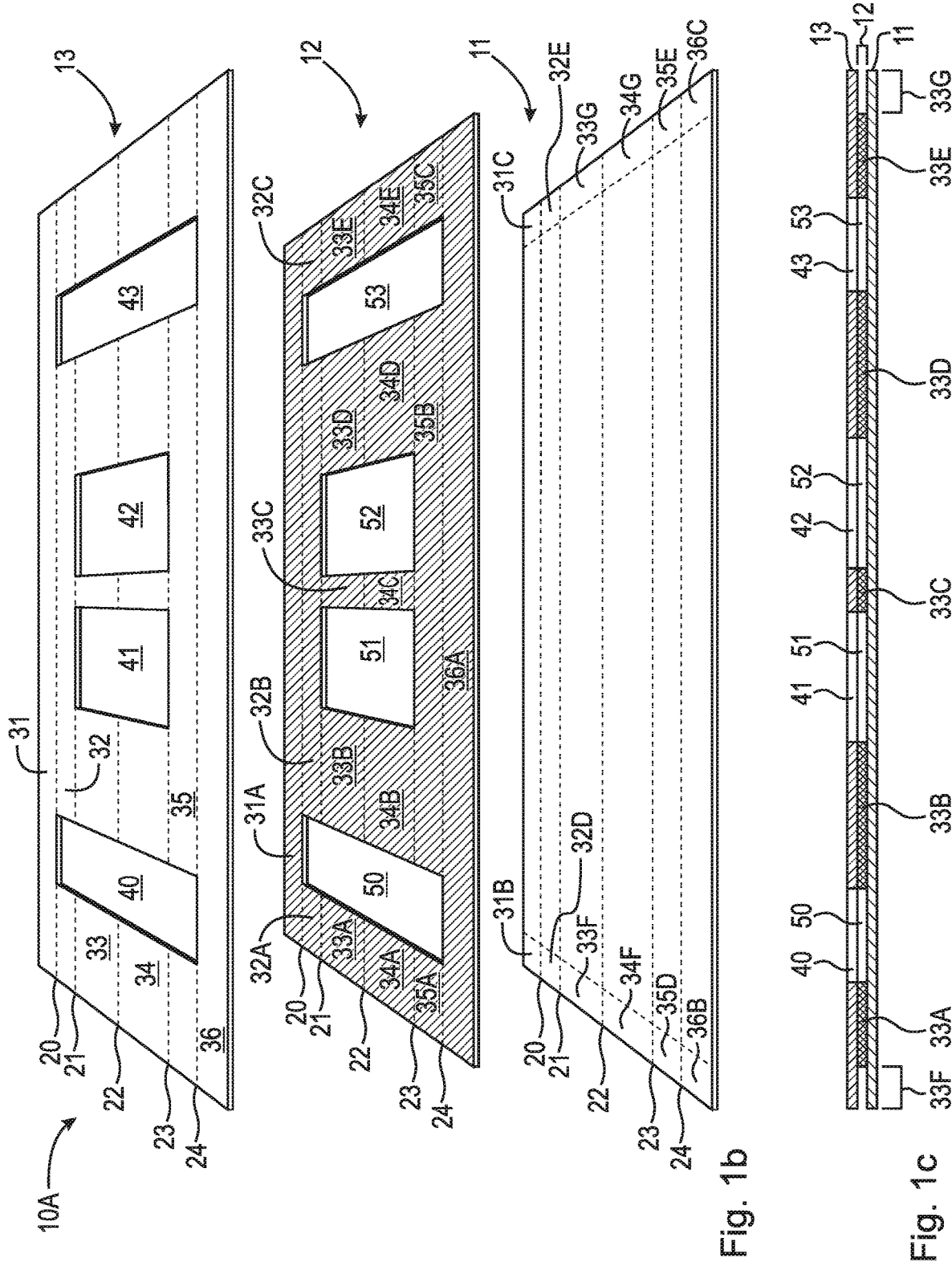

FIG. 1b is a fragmentary exploded view of a first embodiment of assembly 10. Subassembly 10A is the adhesive strip portion of assembly 10. Subassembly 10A includes removable sections 31, 32, 33, 34, 35, and 36, which can be separated from removable sections 38, 38', 39, and 39' along perforation line 25. Also included in subassembly 10A are perforation lines 20, 21, 22, 23, and 24. Removable sections 31, 32, 33, 34, 35, and 36 each include respective portions of transparent non-adhesive substrate 11, transparent adhesive layer 12, and removable layer 13. As shown in FIG. 1b, transparent adhesive layer 12 has adhesive sections 31A, 32A, 32B, 32C, 33A, 33B, 33C, 33D, 33E, 34A, 34B, 34C, 34D, 34E, 35A, 35B, 35C, and 36A. Transparent adhesive layer 12 also has apertures 50, 51, 52, and 53, which are identical in dimension to, and are precisely aligned with, removable layer 13 apertures 40, 41, 42, and 43, respectively. Said apertures represent the absence of material within transparent adhesive layer 12 and removable layer 13, respectively. Removable sections 31, 32, and 33 have substantially similar adhesive sections to that of removable sections 36, 35, and 34, respectively, as assembly 10 is designed to secure two needles. It should be appreciated that transparent adhesive layer 12 is comparable to double-sided adhesive tape in that it has adhesive on both its bottom surface, to which transparent non-adhesive substrate 11 is secured, and also its top surface, to which removable layer 13 secured. In one embodiment, transparent adhesive layer 12 is a double-sided adhesive tape, such as 3M™ 1577 Two in One Double Coated Tape, consisting of a transparent polyester backing, coated on both sides with a hypoallergenic, pressure sensitive, synthetic rubber based adhesive on the face side and a acrylate adhesive on the linear side. To protect the adhesive coating, 3M™ 1577 Double Coated Tape is supplied with silicone treated, bleached Kraft-Glassine paper liners assembled to both surfaces. After apertures are cut into the double-sided adhesive tape, the bottom surface liner is removed and the tape's exposed adhesive surface is secured atop transparent non-adhesive substrate 11. The top surface liner remains assembled as removable layer 13. In a preferred embodiment, removable layer 13 is a translucent. It is important to note that both adhesive side of 3M™ 1577 Double Coated Tape have different adhesive strengths when compared to one another. The synthetic rubber adhesive has greater adhesive strength that the acrylate adhesive. This is to aid in the removal of the tape from a patient's skin when treatment is completed and to reduce the amount of irritation on a patient's skin from the tape. In another embodiment, transparent adhesive layer 12 is a medical adhesive transfer tape, such as 3M™ 1504XL Hi-Tack Transfer Adhesive, consisting of a synthetic rubber-based adhesive supplied in tape form on an extended two-sided siliconized white paper release liner. It should be appreciated, however, that the top surface liner of double-sided adhesive tape and adhesive transfer tape will contain removable layer 13 apertures 40, 41, 42, and 43. Apertures 40, 41, 42, and 43 can be eliminated to promote the easy removal of removable layer 13 after assembly 10 is divided into individual removable sections. Thus, in another embodiment, after the bottom adhesive surface of transparent adhesive layer 12 is secured atop transparent non-adhesive substrate 11, the top surface liner containing apertures 40, 41, 42, and 43 is removed. Removable layer 13, a single continuous liner substantially identical in dimension to transparent non-adhesive substrate 11, is then secured atop transparent adhesive layer 12. In yet another embodiment, transparent adhesive layer 12 is adhesive applied directly atop transparent non-adhesive substrate 11 at the locations shown in FIG. 1b. Any suitable method of applying the adhesive, such as spraying, may be used. In a preferred embodiment, transparent non-adhesive substrate 11 is made of polyester, however, any suitable alternative, such as ethylene vinyl acetate (EVA) or polypropylene, can be used. Also in a preferred embodiment, removable layer 13 is silicone release paper operatively arranged to be removable from transparent adhesive layer 12 while preserving the adhesive top surface of transparent adhesive layer 12. However, removable layer 13 can be any suitable alternative. Moreover, assembly 10 is arranged to be subdivided into corresponding removable sections before detachment of removable layer 13. Removable layer 13 maintains the adhesive strength and sterility, and should be removed immediately before application to prevent contamination.

Assembly 10 further comprises perforated elements 60 and 61 and fabric elements 70 and 71. As shown in FIG. 1a, perforated elements 60 and 61 are positioned within removable sections 38 and 38' of assembly 10, respectively. Fabric elements 70 and 71 are positioned within removable sections 39 and 39' of assembly 10, respectively. Subassembly 10B comprises removable sections 38, 38', 39, and 39', which can be separated from subassembly 10A, comprising removable sections 31, 32, 33, 34, 35, and 36, along perforation line 25. Subassembly 10B also comprises perforation lines 26 and 27. Removable sections 38 and 38' can be separated from removable sections 39 and 39', respectively, along perforation line 26. Removable sections 38 and 39 can be separated from removable sections 38' and 39', respectively, along perforation line 27.

FIG. 1c shows a cross-sectional view of a first example embodiment of assembly 10 taken generally along line 1c-1c shown in FIG. 1a. Assembly 10 comprises, from bottom to top, transparent non-adhesive substrate 11, transparent adhesive layer 12, and removable layer 13. As shown in FIG. 1c, transparent adhesive layer 12 has a width which is smaller than the width of transparent non-adhesive substrate 11 to ensure that removable sections do not have adhesive on flaps. This allows attendants to easily grasp removable sections to readjust during use on patient's arm 1 without removing their gloves. Substantially similar flaps occur on every removable section of assembly 10. Removable section 31 contains flaps 31B and 31C, removable section 32 contains flaps 32D and 32E, removable section 33 contains flaps 33F and 33G, removable section 34 contains flaps 34F and 34G, removable section 35 contains flaps 35D and 35E, and removable section 36 contains flaps 36B and 36C. Additionally, FIG. 1c shows that removable layer 13 apertures 40, 41, 42, and 43 are aligned with transparent adhesive layer 12 apertures 50, 51, 52, and 53, respectively. In one embodiment, apertures are cut into removable layer 13 and transparent adhesive layer 12 before transparent non-adhesive substrate 11 is assembled, but after transparent adhesive layer 12 and removable layer 13 are secured together. This ensures that apertures 40, 41, 42, and 43 are properly aligned with apertures 50, 51, 52, and 53, respectively. Transparent adhesive layer 12 is secured to transparent non-adhesive substrate 11 via adhesive arranged on the bottom surface of transparent adhesive layer 12.

Figure 2:
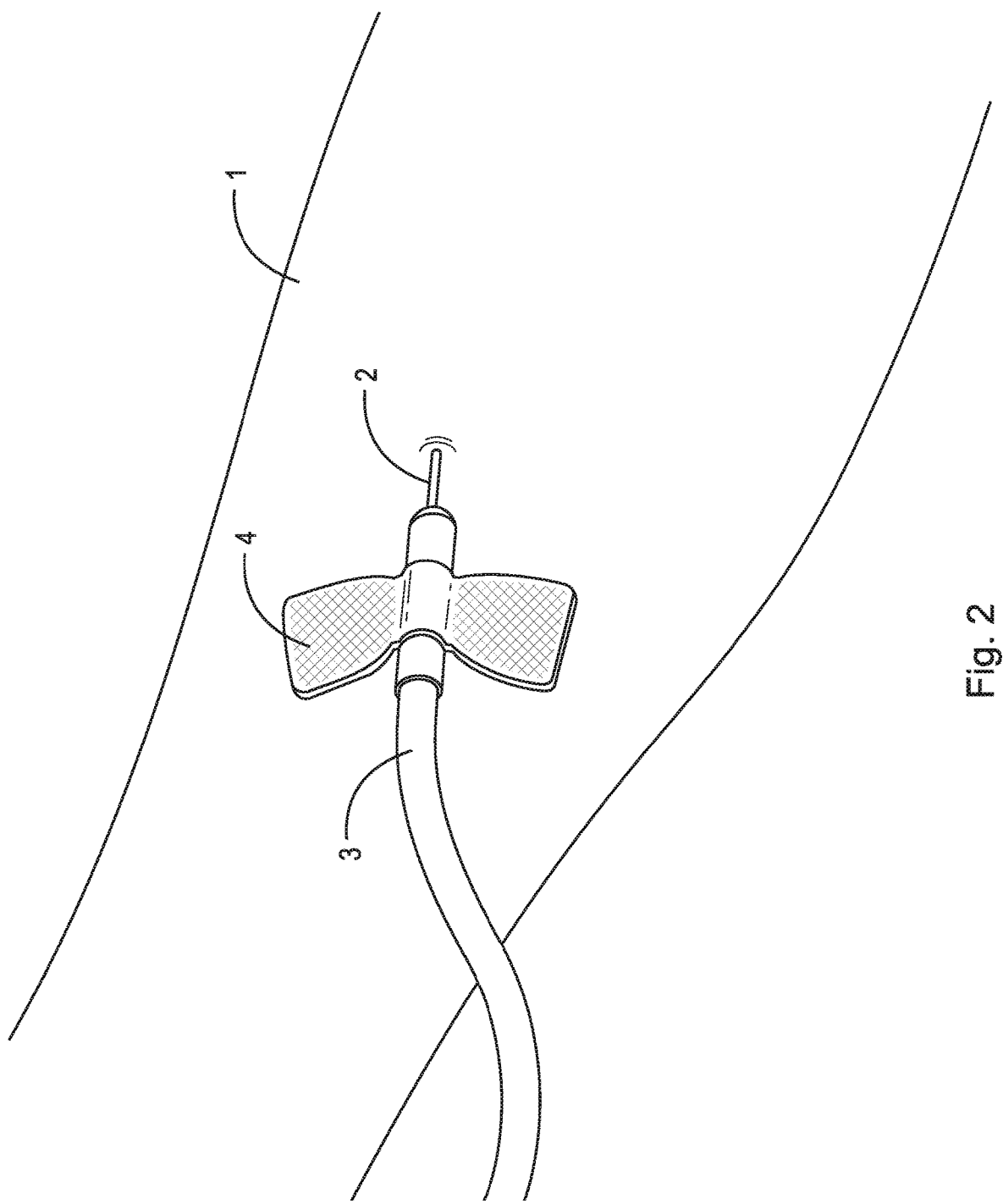
FIG. 2 is a perspective view of a needle within a patient's arm.

FIG. 2 is a perspective view of patient's arm 1 with needle 2 inserted into either a vein or artery, depending on the insertion requirements of the procedure being performed. Also shown in FIG. 2, needle 2 contains wings 4 and tube 3. Typically, infusion needles contain wings to ensure a firm grip during placement. Winged infusion needles often contain flexible wings that can be squeezed together during placement. Once the needle has been inserted, the wings are folded down onto the skin and adhesive tape is placed over the wings. The flexible wings form to the contours of the patient's arm to ensure maximum surface contact, providing surface friction. However, without added pressure or adhesive means, needle 2 will dislodge from patient's arm 1. FIG. 2 shows needle 2 with wings 4 secured in patient's arm 1 by needle 2 only. This arrangement is not suitable. In order to secure needle 2, an attendant must hold needle 2 in patient's arm 1 by applying pressure to wings 4. This application technique is dangerous because holding needle 2 within patient's arm 1 could place additional stress on the injection site, which can cause the patient extreme discomfort and may even cause damage to a vein or artery in the event that needle 2 shifts within patient's arm 1.

Figure 3:
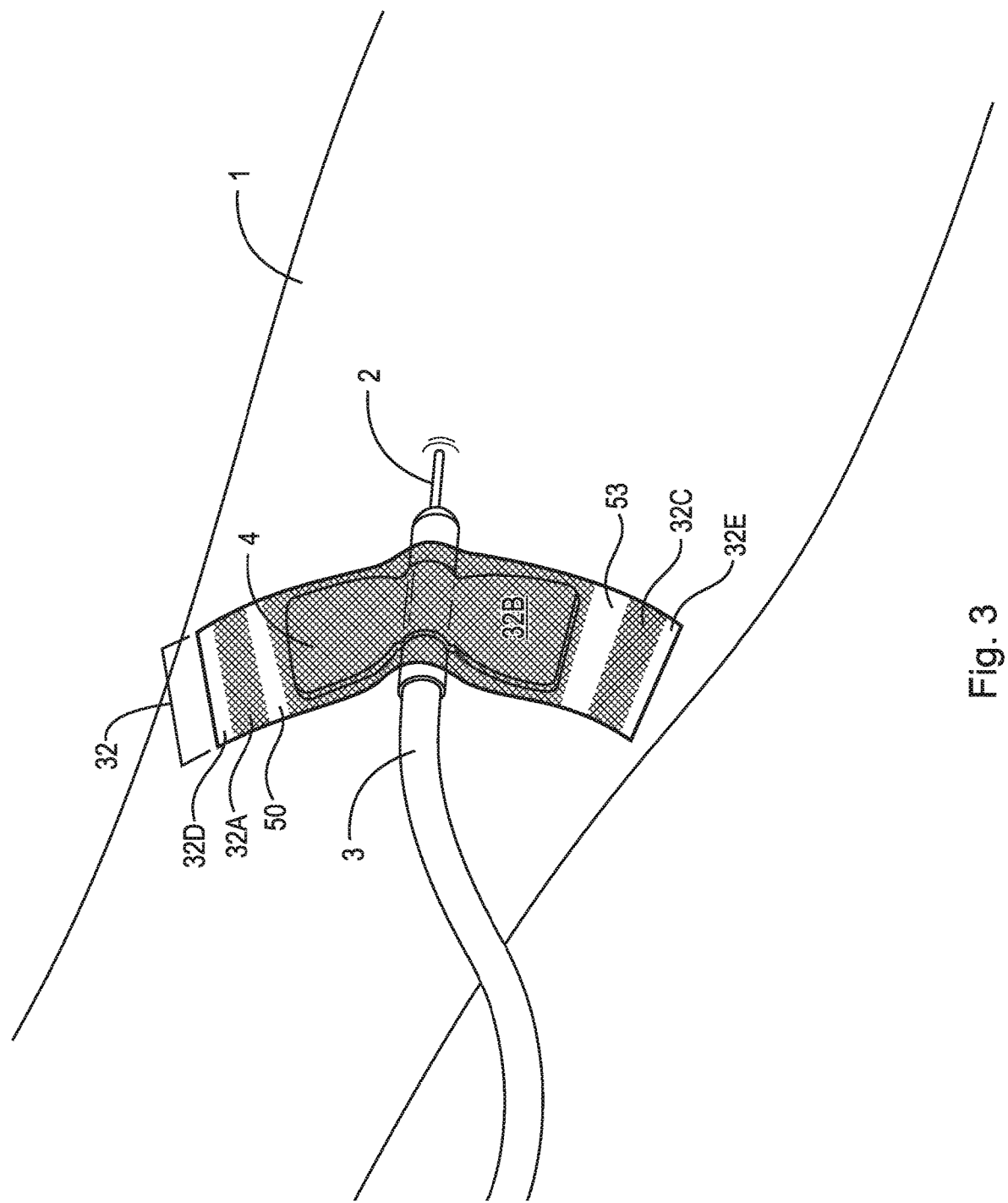
FIG. 3 is a perspective view of the needle secured to the patient's arm shown in FIG. 2 except a transparent strip of the assembly is applied.

FIG. 3 is a perspective view of needle 2 inserted in patient's arm 1 and secured with removable section 32. As shown in FIG. 3, removable section 32 is positioned substantially perpendicular to inserted needle 2, with transparent adhesive layer 12 directed toward patient's arm 1. Removable section 32 comprises adhesive sections 32A, 32B, and 32C with adhesive section 32B securing wings 4 of needle 2. This prevents internal blood pressure from dislodging needle 2 from arm 1. During needle insertion procedures, an attendant removes adhesive strips along perforation lines and applies them to patient's arm 1. Also shown in FIG. 3 are flaps 32D and 32E, and transparent adhesive layer 12 apertures 50 and 53. As shown, transparent adhesive layer 12 does not extend to non-adhesive flaps 32D and 32E, which promotes easy readjustment of adhesive strip 32.

Figure 4:
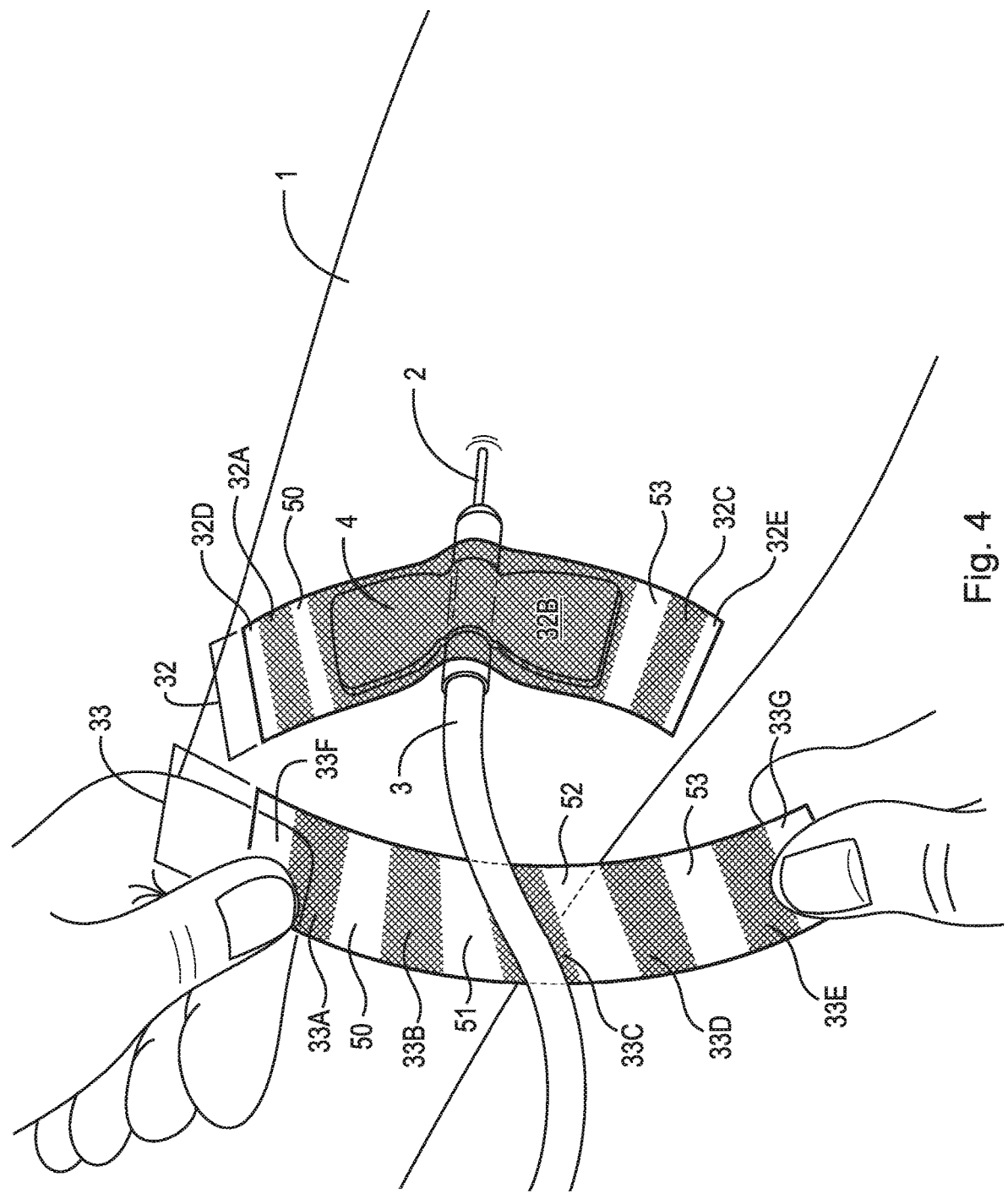
FIG. 4 is a perspective view of the needle secured to the patient's arm shown in FIG. 3 except another transparent strip of the assembly is positioned proximate the patient's arm.

FIG. 4 is a perspective view of needle 2 inserted in patient's arm 1 with removable section 32 securing wings 4 of needle 2. Also shown in FIG. 4 is the application of removable section 33, which is positioned proximate patient's arm 1. Removable section 33 comprises adhesive sections 33A, 33B, 33C, 33D, and 33E with adhesive section 33C securing removable section 33 to tube 3 of needle 2. Removable section 33 is positioned substantially perpendicular to tube 3, with transparent adhesive layer 12 directed away from patient's arm 1. Adhesive section 33C is positioned on the underside of tube 3, opposite the side of tube 3 on which adhesive section 32B is positioned on. An attendant would release removable section 33 from assembly 10 after already positioning removable section 32 on patient's arm 1. An attendant would then position removable section 33 on the underside of tube 3 and position adhesive strip 33 in an appropriate location before applying adhesive section 33C to tube 3.

Figure 5:
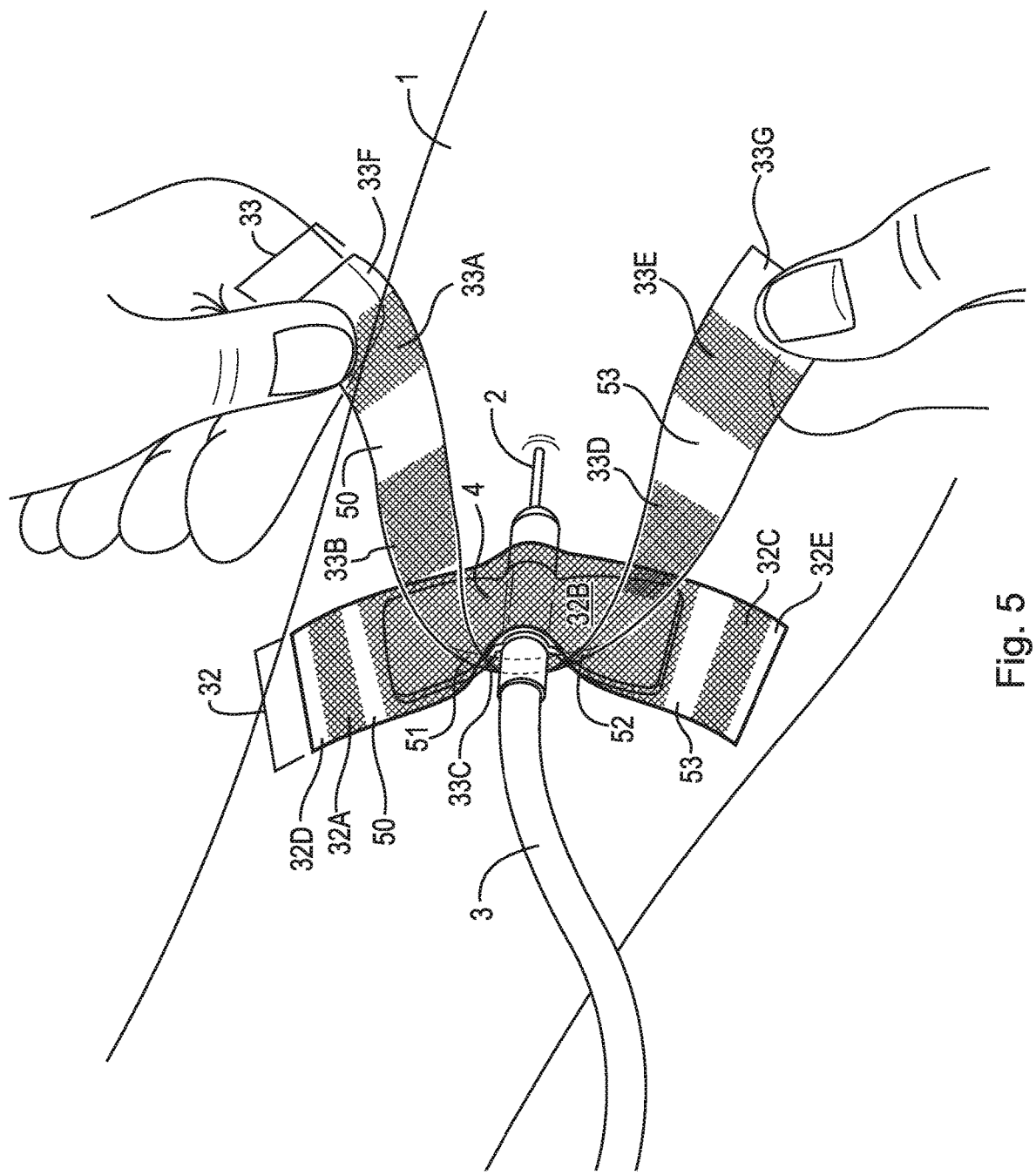
FIG. 5 is a perspective view of the needle assembly shown in FIG. 4, except the transparent strip is further positioned proximate the patient's arm.
Figure 6:
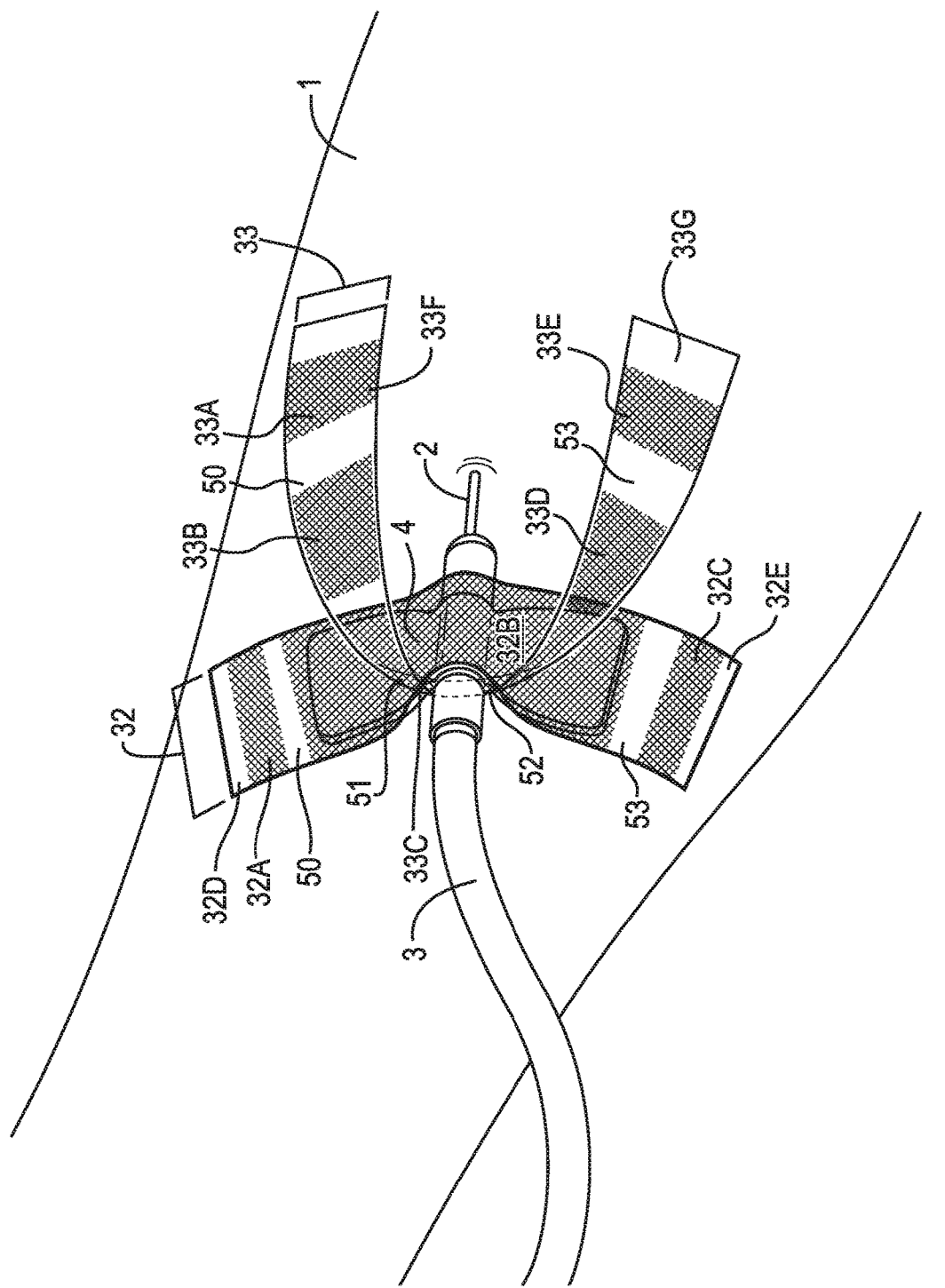
FIG. 6 is a perspective view of the needle secured to the patient's arm shown in FIG. 5 except the transparent strip is adhered to the patent's arm.

FIGS. 5 and 6 are perspective views of needle 2 inserted in patient's arm 1 with adhesive strip 32 securing wings 4 of needle 2 and adhesive strip 33 securing tube 3 of needle 2. As shown in FIG. 5, after an attendant has positioned adhesive section 33C on tube 3, the two distal ends of removable section 33 are positioned around tube 3 and secured on top of adhesive strip 32 forming a chevron shape. It is important to note, however, that removable section 33 can be positioned on a patient's arm 1 to form the chevron shape prior to the securement of removable section 32 on wings 4 of needle 2. The orientation and securement of removable sections 32 and 33 is an extremely important factor for ensuring securement of needle 2 within patient's arm 1. The orientation of removable section 33 under tube 3 prevents rotation of needle 2 within patient's arm 1 during treatment. The placement of the distal ends of removable section 33 provides force that pulls needle 2 forward, into patient's arm 1, to prevent internal pressure from dislodging needle 2 from patient's arm 1. FIG. 6 shows a preferred embodiment of the positioning of adhesive strips 32 and 33 applied proximate patient's arm 1 and needle 2 inserted therein. However, the positioning of removable section 33 on tube 3, the force applied to needle 2 by removable section 33, and the distance with which the distal ends of removable section 33 are spaced apart proximate needle 2 are based on the procedure being performed and the patient's physical characteristics. In a preferred embodiment, removable section 33 would have distal ends positioned in a wide arrangement for a high pressure injection site such as for an artery to ensure needle 2 is fully secured within arm 1. However, if adjustment of needle 2 is necessary, an attendant can grasp removable section 33 at flaps 33F and 33G and reposition the distal ends of adhesive strip 33 in the appropriate locations to ensure proper securement of needle 2 and to maximize patient comfort.

FIG. 7a shows an exploded perspective view of subassembly 10B. Subassembly 10B is the portion of assembly 10 that includes removable sections 38, 38', 39, and 39'. Subassembly 10B broadly includes, from bottom to top, transparent non-adhesive substrate 11, transparent adhesive layer 12, and removable layer 13. Assembly 10 is arranged such that transparent non-adhesive substrate 11 and transparent adhesive layer 12 remain adhesively bonded while removable layer 13 is removed from transparent adhesive layer 12. In a preferred embodiment, transparent non-adhesive substrate 11 is made of polypropylene. Also In a preferred embodiment, removable layer 13 is silicone release paper operatively arranged to be removable from transparent adhesive layer 12 while preserving the adhesive qualities of transparent adhesive layer 12. However, removable layer 13 can be any suitable alternative. Moreover, assembly 10 is arranged to be subdivided into its corresponding removable sections before removable layer 13 is removed from transparent adhesive layer 12.

As shown in FIG. 1a, assembly 10 includes perforation lines to separate assembly 10 into removable sections 38, 38', 39, and 39'. In a preferred embodiment, assembly 10 includes perforation lines 26 and 27. Perforation line 26 separates removable sections 38 and 38' from removable sections 39 and 39', respectively. Perforation line 27 is positioned substantially perpendicular to perforation line 26, and separates removable sections 38 and 39 from removable sections 38' and 39', respectively. It should be appreciated that assembly 10 is divisible into removable sections 38, 38', 39, and 39' while transparent non-adhesive substrate 11, transparent adhesive layer 12, and removable layer 13 remain assembled. Removable sections 38 and 38' are identical and removable sections 39 and 39' are identical, as assembly 10 is designed to secure two needles. Upon removal of each needle, perforated elements 60 and 61 and fabric elements 70 and 71 promote clotting and dressing at the injection sites.

As shown in FIG. 7a, removable sections 38 and 38' include corresponding portions of removable layer 13, adhesive sections 38A and 38A' of transparent adhesive layer 12, and perforated elements 60 and 61 and corresponding portions of transparent non-adhesive substrate 11, respectively. Perforated elements 60 and 61 are located within corresponding portions 38 and 38' of transparent non-adhesive substrate 11, respectively. Removable sections 39 and 39' include corresponding portions of removable layer 13, adhesive sections 39A and 39A' of transparent adhesive layer 12, and fabric elements 70 and 71 and corresponding portions of transparent non-adhesive substrate 11, respectively. Fabric elements 70 and 71 are located within corresponding portions 39 and 39' of transparent non-adhesive substrate 11, respectively. In a preferred embodiment, perforated elements 60 and 61 and fabric elements 70 and 71 are rectangular, with perforated elements 60 and 61 having substantially identical dimensions and fabric elements 70 and 71 having substantially identical dimensions. However, the shape and dimensions of perforated elements 60 and 61 and fabric elements 70 and 71 can be varied. It should be appreciated that transparent adhesive layer 12 is comparable to double-sided tape in that it is adhesive on its bottom surface, to which transparent non-adhesive substrate 11 is attached, and also on its top surface, to which removable layer 13 is attached. Additionally, in a preferred embodiment the perforations of perforated elements 60 and 61 are cuts made into transparent non-adhesive substrate 11 in such a way that they do not have frayed edges such as a stamped out circle. Instead the perforations are cuts made in a '+' shape to ensure material can pass through perforated elements 60 and 61. It should be appreciated, however, that the use of different perforation styles is possible and to be considered within the scope of the claimed invention.

Removable layer 13 includes apertures 44, 45, 46, and 47 and transparent adhesive layer 12 includes apertures 54, 55, 56, and 57. Said apertures represent the absence of material within removable layer 13 and transparent adhesive layer 12, respectively. Apertures 44 and 54 and apertures 45 and 55 are located within removable sections 38 and 38', respectively. Apertures 46 and 56 and apertures 47 and 57 are located within removable sections 39 and 39', respectively. In a preferred embodiment, apertures and elements are rectangular shaped, with apertures 44, 45, 54, and 55 and perforated elements 60 and 61 having substantially identical dimensions, and apertures 46, 47, 56, and 57 and fabric elements 70 and 71 having substantially identical dimensions. It should be appreciated, however, that the use of different shapes for apertures and corresponding elements is possible and to be considered within the claimed invention. Also in a preferred embodiment, apertures 44, 45, 54, and 55 of removable sections 38 and 38' and apertures 46, 47, 56, and 57 of removable sections 39 and 39' are fully contained within the boundaries set by perforation lines 26 and 27. This ensures that when removable layer 13 is removed from transparent adhesive layer 12, an adhesive border completely surrounds perforated elements 60 and 61 and fabric elements 70 and 71. As shown in FIG. 7a, perforated elements 60 and 61 will have adhesive borders provided by adhesive sections 38A and 38A', respectively, and fabric elements 70 and 71 will have adhesive borders provided by adhesive sections 39A and 39A', respectively.

When assembling transparent non-adhesive substrate 11, perforated elements 60 and 61 must be precisely aligned with transparent adhesive layer 12 apertures 54 and 55, respectively, and fabric elements 70 and 71 must be precisely aligned with transparent adhesive layer 12 apertures 56 and 57, respectively. As previously discussed, apertures are created after the bottom surface of removable layer 13 is secured to the top surface of transparent adhesive layer 12. This ensures that removable layer 13 apertures 44, 45, 46, and 47 are precisely aligned with transparent adhesive layer 12 apertures 54, 55, 56, and 57, respectively. To expedite the process of making the invention, assembly 10 is designed so that transparent non-adhesive substrate 11 and removable layer 13 have substantially identical exterior dimensions, and the dimensions and location of apertures 44, 45, 46, and 47 within removable layer 13 are substantially identical to the dimensions and location of elements 60, 61, 70, and 71 within transparent non-adhesive substrate 11, respectively. The top surface of transparent non-adhesive substrate 11 is positioned about the bottom surface of transparent adhesive layer 12 so edges of transparent non-adhesive substrate 11 are precisely aligned with edges of removable layer 13, respectively. Transparent non-adhesive substrate 11 is secured to the bottom surface of transparent adhesive layer 12, ensuring that transparent non-adhesive substrate 11 elements 60, 61, 70, and 71 are aligned with transparent adhesive layer 12 apertures 54, 55, 56, and 57, respectively. Also in a preferred embodiment, apertures 46, 47, 56, and 57 have smaller dimensions than apertures 44, 45, 54, and 55 to ensure that when applied to patient's arm 1, fabric elements 70 and 71 can be completely covered by perforated elements 60 and 61, respectively.

FIGS. 7b and 7c show cross-sectional views of assembly 10 taken generally along lines 7b-7b and 7c-7c shown in FIG. 1a. As shown in FIG. 7b, transparent adhesive layer 12 has dimensions which are smaller than transparent non-adhesive substrate 11 to ensure that removable sections 38 and 38' do not have adhesive on flaps 38B and 38C, or flaps 38B' and 38C', respectively. Similarly, as shown in FIG. 7c, removable sections 39 and 39' have no adhesive on flaps 39B and 39C, or 39B' and 39C', respectively. This lack of adhesive on flaps allows an attendant to easily grasp removable sections 38, 38', 39, and 39' to readjust during use on patient's arm 1 without removing their gloves. Additionally, it can be seen that apertures 44, 45, 46, and 47 of removable layer 13 are aligned with apertures 54, 55, 56, and 57 of transparent adhesive layer 12, respectively. In a preferred embodiment, apertures are cut into removable layer 13 and transparent adhesive layer 12 before transparent non-adhesive substrate 11 is assembled, but while transparent adhesive layer 12 and removable layer 13 are secured together to ensure that apertures are properly aligned.

FIG. 8 is a perspective view of patient's arm 1 properly bandaged. FIG. 9 is a cross-sectional view of patient's arm 1 properly bandaged taken along line 9-9 in FIG. 8. After needle 2 is removed from patient's arm 1, the injection site must be covered to stop excessive bleeding. Using removable sections 38 and 39 of subassembly 10B, the injection site is first covered with removable section 39, containing fabric element 70. Removable section 39 is then covered with removable section 38, containing perforated element 60. Hemostasis element 80 is placed on top of perforated element 60 to reintroduce nutrients into the patient's blood stream. Hemostasis element 80 contains a substance that not only aids in the clotting of blood at the injection site, but also releases vital minerals and nutrients into the patient's blood stream. In a preferred embodiment, hemostasis element 80 is a potato-based mixture used to replenish a patient's calcium and potassium levels, which could be depleted during a procedure. It should be appreciated, however, that other types of substances can be used within hemostasis element 80 and are considered to be within the scope of the invention as claimed. For example, a substance which utilizes Icelandic shrimp shells can be used to promote blood clotting due to the presence of the natural mineral chitosan within the shells. Certain types of rare earth patches and minerals, including zeolite and kaolinite, when properly prepared can have similar hemostatic effects which can be utilized through this invention. Additionally, a black pepper-based, or cayenne pepper-based, substance could be used to promote blood clotting. Once hemostasis element 80 is placed on top of perforated element 60, removable section 31 is placed over the top of hemostasis element 80 to secure it until blood clotting occurs. Assembly 10 is designed for two uses, and includes enough fabric elements, perforated elements, and adhesive sections to support securement of two injected needles and promote clotting and dressing of the injection site after the needles are removed.

In another embodiment, removable section 39 containing fabric element 70 and hemostasis element 80 can be combined by putting hemostat products within fabric element 70. In a preferred embodiment, fabric element 70 would be a gauze pad which contained a surgical hemostat such as Vitagel™. Vitagel™ includes the biological component thrombin, an enzyme that assists in the clotting of blood when conventional means fail or are impractical. This would allow the hemostasis element 80 to be directly applied to a patient's skin where a needle was used and clot the blood faster than traditional means. Additionally, assembly 10 is sterilized after assembly of each component to ensure infection does not spread to a patient. The methods for sterilizing assembly 10 include, but are not limited to, gamma ray, x-ray, and electron beam sterilization.

FIG. 10a and FIG. 10b are a fragmentary exploded view and a cross-sectional view of a second embodiment of the assembly, respectively. In the second example embodiment of assembly 10, transparent adhesive layer 12 does not contain apertures 50, 51, 52, and 53. Instead, transparent adhesive layer 12 completely covers transparent non-adhesive substrate 11 except for non-adhesive flaps 31B, 31C, 32D, 32E, 33F, 33G, 34F, 34G, 35D, 35E, 36B, and 36C. Adhesive blockers 90, 91, 92, and 93 are operatively arranged on transparent adhesive layer 12. The placement of adhesive blockers 90, 91, 92, and 93 creates adhesive sections 31A, 32A, 32B, 32C, 33A, 33B, 33C, 33D, 33E, 34A, 34B, 34C, 34D, 34E, 35A, 35B, 35C, and 36A and non-adhesive sections 90A, 91A, 92A, and 93A covered by adhesive blockers 90, 91, 92, and 93. The addition of adhesive blockers 90, 91, 92, and 93 does not alter the function of the second embodiment of assembly 10 when compared to the first embodiment of assembly 10.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS 1 patient's arm
2 needle
3 tube
4 wings
10 assembly
10A subassembly
10B subassembly
11 transparent non-adhesive substrate
12 transparent adhesive layer
13 removable layer
20 perforation line
21 perforation line
22 perforation line
23 perforation line
24 perforation line
25 perforation line
26 perforation line
27 perforation line
31 removable section
31A adhesive section
31B non-adhesive flap
31C non-adhesive flap
32 removable section
32A adhesive section
32B adhesive section
32C adhesive section
32D non-adhesive flap
32E non-adhesive flap 33 removable section
33A adhesive section
33B adhesive section
33C adhesive section
33D adhesive section
33E adhesive section
33F non-adhesive flap
33G non-adhesive flap
34 removable section
34A adhesive section
34B adhesive section
34C adhesive section
34D adhesive section
34E adhesive section
34F non-adhesive flap
34G non-adhesive flap
35 removable section
35A adhesive section
35B adhesive section
35C adhesive section
35D non-adhesive flap
35E non-adhesive flap
36 removable section
36A adhesive section
36B non-adhesive flap
36C non-adhesive flap
38 removable section
38A adhesive section
38B non-adhesive flap
38C non-adhesive flap
38' removable section
38A' adhesive section
38B' non-adhesive flap
38C' non-adhesive flap
39 removable section
39A adhesive section
39B non-adhesive flap
39C non-adhesive flap
39' removable section
39A' adhesive section
39B' non-adhesive flap
39C' non-adhesive flap
40 aperture
41 aperture
42 aperture
43 aperture
44 aperture
45 aperture
46 aperture
47 aperture
50 aperture
51 aperture
52 aperture
53 aperture
54 aperture
55 aperture
56 aperture
57 aperture
60 perforated element
61 perforated element
70 fabric element
71 fabric element
80 hemostasis element
90 adhesive blocker
91 adhesive blocker
92 adhesive blocker
93 adhesive blocker
90A non-adhesive section
91A non-adhesive section
92A non-adhesive section
93A non-adhesive section

What is claimed is:

1. A securement device assembly, comprising:
an adhesive layer having a top surface and a bottom surface, wherein said adhesive layer includes at least two apertures, wherein a first aperture of the at least two apertures is bounded by an outer perimeter of the adhesive layer;
a non-adhesive substrate secured to said bottom surface of said adhesive layer to form an integral unit; and,
a plurality of perforations within said integral unit, wherein at least one perforation of the plurality of perforations extends through the first aperture and is operatively arranged to separate the first aperture into at least two portions.

2. The securement device assembly as recited in claim 1, wherein said integral unit further comprises a removable layer secured to said top surface of said adhesive layer.

3. The securement device assembly as recited in claim 2, wherein said non-adhesive substrate and said removable layer have a first width and said adhesive layer has a second width, wherein said second width is less than said first width.

4. The securement device assembly as recited in claim 1, wherein said plurality of perforations are arranged in parallel lines dividing said integral unit into a plurality of strips.

5. The securement device assembly as recited in claim 1, wherein said perforations divide said integral unit into a first strip, a second strip, a third strip, a fourth strip, a fifth strip, and a sixth strip, wherein said first strip is substantially similar to said sixth strip, said second strip is substantially similar to said fifth strip, and said third strip is substantially similar to said fourth strip.

6. The securement device assembly as recited in claim 1, wherein said non-adhesive substrate is made of polypropylene.

7. The securement device assembly as recited in claim 1, wherein said non-adhesive substrate is made of polyester.

8. The securement device assembly as recited in claim 1, wherein said securement device is sterile.

9. The securement device assembly as recited in claim 8, wherein said securement device is sterilized by gamma ray sterilization.

10. The securement device assembly as recited in claim 8, wherein said securement device is sterilized by x-ray sterilization.

11. The securement device assembly as recited in claim 8, wherein said securement device is sterilized by electron beam sterilization.

12. The securement device assembly as recited in claim 1, wherein said adhesive layer is transparent.

13. The securement device assembly as recited in claim 1, wherein said non-adhesive substrate is transparent.

14. A securement and dressing device assembly, comprising:
an adhesive layer having a top surface and a bottom surface, wherein said adhesive layer includes at least two apertures;
a non-adhesive substrate, comprising:
at least one absorption element secured to said non-adhesive substrate, and arranged in registration with a first of said apertures; and,
at least one permeable element secured to said non-adhesive substrate, and arranged in registration with a second of said apertures;

wherein said non-adhesive substrate is secured to said bottom surface of said adhesive layer to form an integral unit; and, a plurality of perforations arranged within said integral unit, wherein at least one perforation of the plurality of perforations separates the at least one absorption element and the at least one permeable element.

15. The securement and dressing device assembly as recited in claim 14, wherein said integral unit further comprises a removable layer secured to said top surface of said adhesive layer.

16. The securement and dressing device assembly as recited in claim 15, wherein said non-adhesive substrate and said removable layer have a first width and said adhesive layer has a second width, wherein said second width is less than said first width.

17. The securement and dressing device assembly as recited in claim 15, wherein said non-adhesive substrate is made of polyester.

18. The securement and dressing device assembly as recited in claim 14, wherein said absorption element is at least partially aligned with a first non-adhesive portion of said adhesive layer, and said permeable element is at least partially aligned with a second non-adhesive portion of said adhesive layer.

19. A method for securing a needle assembly to a surface using a tape assembly, the method comprising the steps of:
   inserting said needle assembly through said surface and into a vessel thereunder, said needle assembly comprising a tube, a needle connected to said tube, and a wing connected to said tube proximate the needle;
   adhering a first adhesive section of a first strip of material under said tube proximate said wing, wherein said first strip of material includes a first end and a second end, and the first adhesive section is arranged between a first non-adhesive section and a second non-adhesive section;
   folding said first end and said second end of said first strip of material such that said first and second ends traverse said wing;
   adhering said first and second ends of said first strip of material to said surface; and,
   adhering a second strip of material atop of said wing and said first strip of material.

20. The method recited in claim 19, further comprising arranging said first and second ends of said first strip of material such that the first strip of material forms a chevron.

21. The method recited in claim 19, wherein the step of folding said first end and said second end of said first strip of material such that said first and second ends traverse said wing further comprises:
   arranging said first strip of material such that the first and second ends extend outward from said tube and never cross each other.

22. The method recited in claim 19, wherein the step of adhering a second strip of material atop of said wing and said first strip of material comprises:
   adhering a second adhesive section of the second strip of material to the first strip of material and/or the tube, wherein the second adhesive section is arranged between a third non-adhesive section and a fourth non-adhesive section.

23. The method as recited in claim 19, wherein said second strip of material is substantially perpendicular to said tube of said needle assembly.

24. A securement and dressing device assembly, comprising:
   an adhesive layer having a top surface and a bottom surface, wherein said adhesive layer includes at least two apertures;
   a non-adhesive substrate secured said bottom surface of said adhesive layer to form an integral unit; and,
   a plurality of perforations operatively arranged within said integral unit, said plurality of perforations forming a first portion having a plurality of removable strips and a second portion having at least one absorption element and at least one permeable element.

25. The securement device assembly as recited in claim 24, wherein said adhesive layer is transparent.

26. The securement device assembly as recited in claim 24, wherein said non-adhesive substrate is transparent.

27. The securement and dressing device assembly recited in claim 24, wherein said absorption method is made of gauze.

28. The securement and dressing device assembly recited in claim 24, wherein said first portion includes a first strip, a second strip, a third strip, a fourth strip, a fifth strip, and a sixth strip, wherein said first strip is substantially similar to said sixth strip, said second strip is substantially similar to said fifth strip, and said third strip is substantially similar to said fourth strip.

29. The securement and dressing device assembly as recited in claim 24, wherein said second portion includes a first absorption element, a second absorption element, a first permeable element, and a second permeable element, wherein said first and second absorption elements are substantially similar, and said first and second permeable elements are substantially similar.

30. A securement device assembly, comprising:
   a non-adhesive substrate having a first top surface and a first bottom surface;
   an adhesive layer having a second top surface and a second bottom surface, said adhesive layer secured to said first top surface along said second bottom surface;
   a plurality of adhesive blockers arranged on the second top surface, wherein the non-adhesive substrate, the adhesive layer, and the plurality of adhesive blockers form an integral unit; and,
   a plurality of perforations within said integral unit separating said integral unit into a plurality of sections.

31. The securement device assembly recited in claim 30, wherein said integral unit comprises a plurality of non-adhesive flaps.

32. The securement device assembly as recited in claim 30, wherein said integral unit further comprises a removable layer secured to said second top surface.

* * * * *

UNITED STATES PATENT AND TRADEMARK OFFICE
CERTIFICATE OF CORRECTION

| | | |
|---|---|---|
| PATENT NO. | : 10,758,671 B2 | Page 1 of 1 |
| APPLICATION NO. | : 15/584689 | |
| DATED | : September 1, 2020 | |
| INVENTOR(S) | : Dennis Tollini and Michael Tollini | |

It is certified that error appears in the above-identified patent and that said Letters Patent is hereby corrected as shown below:

On the Title Page

Item (73) Assignee should be corrected to read:
"TNT Moborg International Limited"

Signed and Sealed this
Twentieth Day of October, 2020

Andrei Iancu
*Director of the United States Patent and Trademark Office*